United States Patent [19]

Ludwig

[11] 4,306,452
[45] Dec. 22, 1981

[54] CALORIMETER

[76] Inventor: Klaus F. Ludwig, 406 Northumberland Ave., North Riding, Randburg, Transvaal, South Africa

[21] Appl. No.: 105,975

[22] Filed: Dec. 21, 1979

[30] Foreign Application Priority Data

Sep. 26, 1979 [ZA] South Africa ...................... 79/5101

[51] Int. Cl.³ ............................................ G01K 17/00
[52] U.S. Cl. ..................................................... 73/191
[58] Field of Search ............................. 73/191, 190 R; 23/230 PC

[56] References Cited

U.S. PATENT DOCUMENTS 3,451,267 6/1969 Wiegert et al. ....................... 73/191
4,130,016 12/1978 Walker ................................ 73/190 R

*Primary Examiner*—Jerry W. Myracle
*Attorney, Agent, or Firm*—McAulay, Fields, Fisher, Goldstein & Nissen

[57] ABSTRACT

This invention relates to a method of and apparatus for determining the calorific value of a sample of combustible material. The apparatus consists of a calorimeter bomb which is located in a temperature insulated enclosure and includes temperature sensors which are located in the wall of the bomb with electrical terminals for firing the bomb and monitoring the temperature changes in the wall of the bomb passing through the base of the bomb and enclosure for connection to a computer. The method consists in monitoring temperature changes in the wall of the bomb when it has been fired to burn a sample located in it by means of a computer.

9 Claims, 1 Drawing Figure

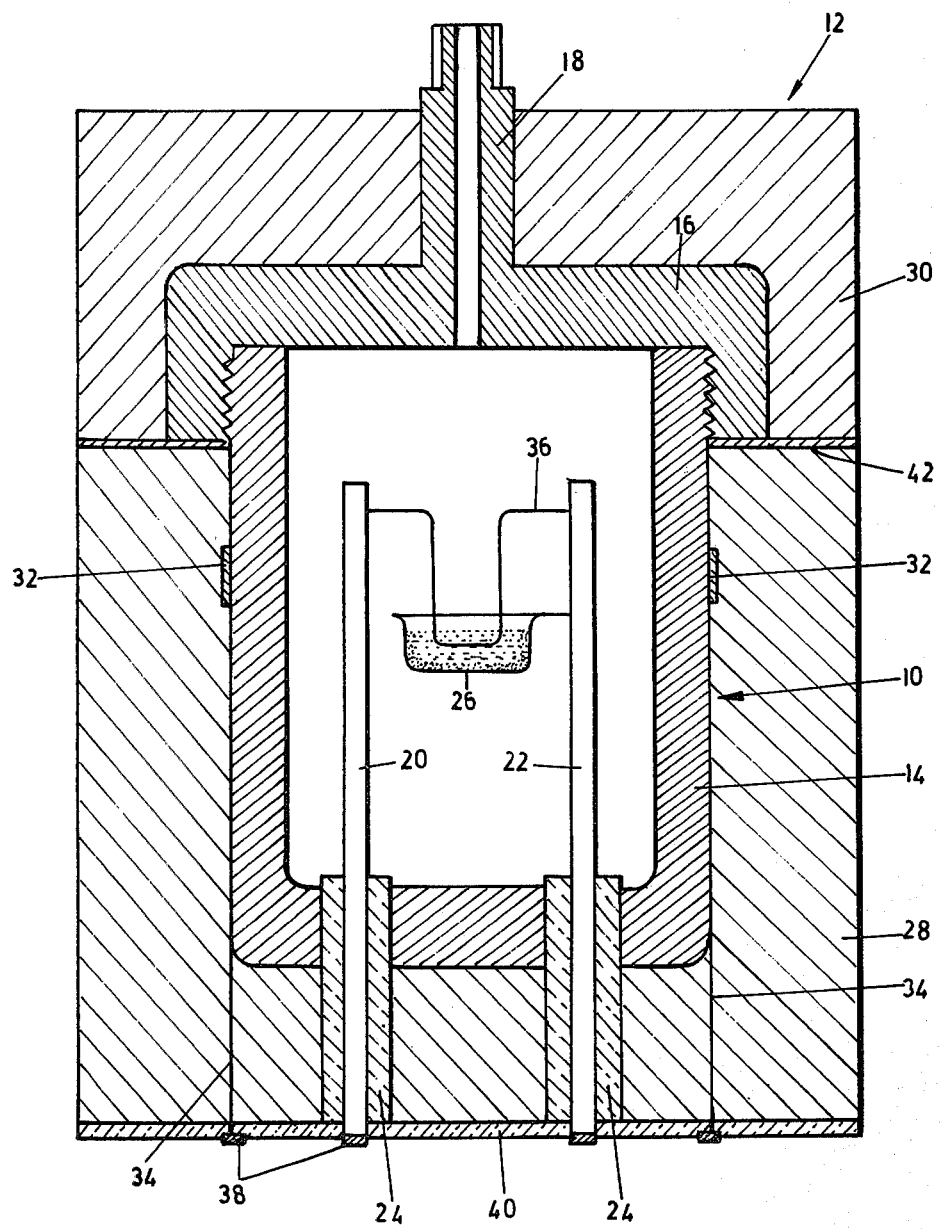

CALORIMETER

FIELD OF THE INVENTION

This invention relates to a method of and apparatus for determining the gross calorific value of solid or liquid combustible substances.

BACKGROUND TO THE INVENTION

Calorific measurements have for many years been carried out by means of either adiabatic or isothermal bomb calorimeter systems. Both of these systems employ a bomb in which the sample of material to be tested is burnt in oxygen under high pressure, a calorimeter vessel in which the bomb is immersed in water, temperature measuring means in the water and a stirrer for circulating the water in the vessel. In the isothermal system the calorimeter vessel is located within an isothermal stirred water jacket from which it is insulated by an air space and in the adiabatic system the vessel and bomb are located in a stirred water jacket which completely surrounds and is separated from the vessel by an air space.

In both systems it is necessary to provide elaborate means for controlling the water jacket temperature. With the isothermal system it is necessary to maintain a substantially constant jacket temperature and with the adiabatic system the temperature controlling means must be capable of rapidly adjusting the jacket temperature to eliminate temperature differentials between the jacket and calorimeter for accurate adiabatic operation.

Because of the high degree of accuracy necessary from control systems such as heaters, stirrers and the like and the number of measurable variables such as water quantities and temperatures which have to be accurately and constantly measured and monitored during the testing of a sample, the systems are cumbersome and time consuming to operate. Additionally, because of the number of variables which have constantly to be monitored and errors which they themselves introduce to the system, and this includes ambient temperatures variations in which the systems are operated, the accuracy of the results of the tests using these systems are often questionable.

OBJECT OF THE INVENTION

It is the object of this invention to provide both a method and apparatus for determining the calorific value of a combustible sample which will minimize the above difficulties with known measuring systems.

SUMMARY OF THE INVENTION

A method of measuring the calorific value of a sample of combustible material according to the invention consists in the steps of locating a sample of the material to be tested in a calorimeter bomb housing which includes at least one but preferably a plurality of temperature sensors located in the wall of the housing, igniting the sample, and measuring the temperature change over a period of time in the material of the wall of the housing.

Conveniently, the bomb housing is in operation located in a temperature insulated housing which may consist of an isothermal or adiabatic jacket or in its simplest form an enclosure made from a heat insulating foamed plastics material.

Apparatus for measuring the calorific value of a sample of combustible material according to the invention includes a calorimeter bomb and at least one temperature sensor located in the material of the wall of the bomb.

Preferably, the bomb consists of a container of stainless steel or like pressure and corrosion resistant material and an outer heat sink jacket of heat conductive material which is suitably bonded to the container for heat transfer between the materials of the two components.

In one form of the invention the housing includes a plurality of temperature sensors which are located between and in contact with both the container and its jacket.

BRIEF DESCRIPTION OF THE DRAWING

An embodiment of the invention is now described by way of example with reference to the drawing which is a sectioned side elevation of the calorimeter of the invention.

DETAILED DESCRIPTION OF THE PREFERRED EMBODIMENT

The calorimeter of the invention is shown in the drawing to consist essentially of a container 10 and a jacket 12.

The container 10 is substantially identical to a conventional calorimeter bomb and is shown in the drawing to include a thick walled stainless steel container 14, a screw on closure member 16, a filler spigot 18 and two spaced electrodes 20 and 22. The bore of the spigot includes a one way safety/filler valve which is not shown in the drawing. The electrodes 20 and 22 pass through the base of the container 10 in insulators 24. A crucible 26 is attached to the electrode 22 and held co-axially in the container between the electrodes.

Both the container 10 and its closure member 16 are suitably bonded for maximum heat transfer to heavy heat sink components 28 and 30 respectively of the jacket 12. The components 28 and 30 could be made from any suitable highly heat conductive material such as copper, aluminum or the like and to minimize their mass could include sealed cavities, not shown, which are filled with a suitable heat conductive gas under pressure.

Suitable heat sensors 32 which may be of the semiconductor or platinum resistance type are located between the container wall and jacket component 28 in intimate contact with the material of both. Suitable electrically and heat insulated connections 34 are connected to the sensors 32 and pass through the base of the jacket member 28 to be connected, as are the electrodes 20 and 22, to electrically conductive slip rings or segments of slip rings 38 which are located in a base member 40 which is made from electrically insulating material.

In use, the container 10 is charged in the conventional manner by placing a screened and weighted sample of the material to be tested in the crucible 26, connecting a fuse wire 36 between the electrodes and into the sample, adding a small quantity of water to the container and screwing the closure member 16 and its jacket component 38 onto the lower portion of the assembly. A washer 42 of suitable pressure deformable material which is at least as heat conductive as the material from which the jacket is made is located and clamped between the upper and lower components of the assembly to ensure complete heat transfer between the jacket components. The container is then charged through the spigot 18 with oxygen to a pressure of about 3 MPA (420 psi).

The entire calorimeter as described above is then located in a temperature insulated enclosure which may consist of a conventional isothermal or adiabatic jacket or preferably an enclosure made from high density polystyrene.

The upper surface of the base of the enclosure includes suitable contacts which when the calorimeter is fully located in the enclosure make electrical contact with the slip rings 38.

A computer is connected to the contacts in the enclosure and automatically measures and records the temperature behaviour of the calorimeter. When the temperature of the calorimeter in the enclosure has stabilized the temperature is stored in computer memory and the bomb is fired automatically.

The rate and degree of temperature rise in the wall of the calorimeter is monitored by the computer which applies sulphur, moisture, nitric acid, cotton, firing wire, temperature sensor reactions and other corrections to the readings to arrive at the final net temperature determination. The net temperature rise is then multiplied by the previously determined heat equivalent (bomb factor) to arrive at the energy content or calorific value of the material under test.

The calorimeter is then removed from the enclosure and the oxygen under pressure discharged. The calorimeter is then cleaned and placed in a heat conductive cooler which is brought into thermal contact with the outer surfaces of the calorimeter and cooled by circulating water to dissipate heat gained during the test.

The invention is not limited to the precise constructional details as herein described and for fast and accurate calibration of the calorimeter a suitable heater could be embedded in the jacket material or sandwiched between the wall of the container 10 and its heat sink jacket. With this arrangement the method would, prior to firing of the bomb, include the steps of applying known energy to the calorimeter by means of the heater and measuring the resultant temperature rise. This parameter is then compared to the previously determined stabilized temperature of the calorimeter to determine the heat equivalent of the calorimeter which is stored in the computer memory.

From what has been said above it will be appreciated that because of the rapid heat transfer across the container and jacket interface calorific measurements will be able to be made far more rapidly than in the known systems. Further advantages provided by the calorimeter of the invention over the known systems are that it may be simply and accurately calibrated because of the substantially constant heat equivalent of the system and the temperature equalization of the system is considerably faster due to fewer heat transfer surfaces.

I claim:

1. A method of measuring the calorific value of a sample of combustible material consists in locating a sample of the material to be tested in a calorimeter bomb housing which includes a plurality of temperature sensors located in the wall of the housing, igniting the sample, and measuring the temperature change in the wall of the housing over a period of time by means of the sensors, the calorimeter being located in a temperature insulated housing during ignition of the sample and the period in which the temperature change in the wall of the housing is measured.

2. A method as claimed in claim 1 including the steps, prior to the ignition of the sample, of measuring the stabilized temperature of the wall of the calorimeter housing, introducing a specific heat energy into the wall of the housing and measuring the resultant temperature change in the wall of the housing and then determining the heat equivalent of the calorimeter by comparing the stabilized temperature with the change in wall temperature over a period of time.

3. A method as claimed in claim 2 in which electrical conductors are connected between the sample igniting means and the temperature sensors in the wall of the housing and electrical terminals on the outside of the housing and the method includes the steps of connecting a computer to the terminals and carrying out the temperature measurements and ignition of the sample by means of the computer.

4. Apparatus for measuring the calorific value of a sample of combustible material including a calorimeter bomb housing which consists of an inner container which is bonded in intimate thermal transfer contact to an outer heat sink casing of thermally conductive material and at least one temperature sensor located in the material of the wall of the housing.

5. Apparatus as claimed in claim 4 in which the or each heat sensor is located between the walls of the container and heat sink casing.

6. Apparatus as claimed in claim 5 in which electrical leads are connected between means in the housing for igniting the sample, the temperature sensors in the wall of the housing and electrical terminals on the outside of the housing.

7. Apparatus as claimed in claim 6 in which the terminals are slip rings or segments of slip rings on the underside of the housing.

8. Apparatus as claimed in claim 6 including a temperature insulated container in which the calorimeter housing is located while the calorific value of the sample is being determined and a computer which is connected through electrical contacts in the insulated container to the terminals on the housing for automatically carrying out temperature measurements of the wall of the housing and ignition of the sample.

9. Apparatus as claimed in claim 4 in which a heater element is located in the wall of the housing for temperature calibration of the housing.

* * * * *